US012558477B2

(12) United States Patent

McCaffrey

(10) Patent No.: US 12,558,477 B2
(45) Date of Patent: Feb. 24, 2026

(54) DRUG DELIVERY DEVICE INCLUDING RESERVOIR WITH FLEXIBLE LINING

(71) Applicant: Insulet Corporation, Acton, MA (US)

(72) Inventor: Maureen McCaffrey, Arlington, MA (US)

(73) Assignee: INSULET CORPORATION, Acton, MA (US)

( * ) Notice: Subject to any disclaimer, the term of this patent is extended or adjusted under 35 U.S.C. 154(b) by 718 days.

(21) Appl. No.: 17/531,326

(22) Filed: Nov. 19, 2021

(65) Prior Publication Data

US 2022/0168500 A1     Jun. 2, 2022

Related U.S. Application Data

(60) Provisional application No. 63/120,349, filed on Dec. 2, 2020.

(51) Int. Cl.
*A61M 5/142* (2006.01)
*A61M 5/168* (2006.01)

(52) U.S. Cl.
CPC .... *A61M 5/14244* (2013.01); *A61M 5/16809* (2013.01); *A61M 5/16881* (2013.01); *A61M 2205/0266* (2013.01)

(58) Field of Classification Search
CPC .............. A61M 5/142; A61M 5/14248; A61M 5/14586; A61M 5/14593; A61M 5/152;
(Continued)

(56) References Cited

U.S. PATENT DOCUMENTS

| | | | | | |
|---|---|---|---|---|---|
| 4,626,244 | A | * | 12/1986 | Reinicke | A61M 5/141 604/141 |
| 4,741,733 | A | * | 5/1988 | Winchell | A61M 5/141 604/514 |

(Continued)

FOREIGN PATENT DOCUMENTS

| | | |
|---|---|---|
| CN | 107096091 A | 8/2017 |
| EP | 0789146 A1 | 8/1997 |

(Continued)

OTHER PUBLICATIONS

International Search Report and Written Opinion, Application No. PCT/US2022/016713, mailed Aug. 5, 2022, 19 pages.
(Continued)

*Primary Examiner* — Courtney B Fredrickson
*Assistant Examiner* — Kayla M. Turkowski
(74) *Attorney, Agent, or Firm* — GOODWIN PROCTER LLP

(57) ABSTRACT

Embodiments of the present disclosure relate to techniques, processes, devices or systems for pump devices for providing a fixed volume of fluid, which is delivered and refilled within one pumping cycle. In one approach, a wearable drug delivery device may include a reservoir configured to store a liquid drug, and a drive mechanism coupled to the reservoir for receiving the liquid drug. The drive mechanism may include a housing defining a chamber, the housing including an inlet valve operable to receive the liquid drug and an outlet valve operable to expel the liquid drug from the chamber, and a resilient sealing member within the chamber. The drive mechanism may further include a shape memory wire coupled to the resilient sealing member, wherein the shape memory wire is operable to bias the resilient sealing member within the chamber.

8 Claims, 15 Drawing Sheets

(58) Field of Classification Search
CPC .... A61M 2205/0266; A61M 2209/045; A61M
5/14244; A61M 5/148; A61M 5/14224;
B65D 83/0061
See application file for complete search history.

(56) References Cited

U.S. PATENT DOCUMENTS

| | | | |
|---|---|---|---|
| 4,991,743 A | | 2/1991 | Walker |
| 5,135,497 A | * | 8/1992 | Hessel ................ B67D 1/0001 |
| | | | 222/94 |
| 5,167,633 A | * | 12/1992 | Mann ................ A61M 5/14276 |
| | | | 604/141 |
| 5,368,570 A | | 11/1994 | Thompson et al. |
| 5,906,592 A | * | 5/1999 | Kriesel ................ A61M 5/152 |
| | | | 604/890.1 |
| 6,740,059 B2 | | 5/2004 | Flaherty |
| 7,137,964 B2 | | 11/2006 | Flaherty |
| 7,303,549 B2 | | 12/2007 | Flaherty |
| 8,734,396 B2 | | 5/2014 | Wyss |
| 11,583,627 B1 | * | 2/2023 | Forouzandeh .... A61M 5/14276 |
| 2003/0198558 A1 | | 10/2003 | Nason et al. |
| 2004/0115068 A1 | | 6/2004 | Hansen et al. |
| 2006/0259016 A1 | * | 11/2006 | Steinbach ......... A61M 5/14276 |
| | | | 604/891.1 |
| 2007/0255260 A1 | | 11/2007 | Haase |
| 2011/0108158 A1 | | 5/2011 | Huwiler et al. |
| 2011/0319814 A1 | | 12/2011 | Sullivan et al. |
| 2012/0215180 A1 | * | 8/2012 | Halili ................ A61M 5/14248 |
| | | | 604/246 |
| 2013/0324928 A1 | * | 12/2013 | Kruse ............... A61M 5/16854 |
| | | | 604/151 |
| 2015/0032051 A1 | * | 1/2015 | Brandt .............. A61M 5/14276 |
| | | | 604/143 |
| 2016/0144102 A1 | * | 5/2016 | Montalvo ......... A61M 5/14244 |
| | | | 604/123 |
| 2017/0290975 A1 | | 10/2017 | Barmaimon et al. |

FOREIGN PATENT DOCUMENTS

| | | |
|---|---|---|
| EP | 1065378 A2 | 1/2001 |
| EP | 2229970 A1 | 9/2010 |
| EP | 2556815 A1 | 2/2013 |
| WO | 2012065780 A2 | 5/2012 |
| WO | 2013149186 A1 | 10/2013 |

OTHER PUBLICATIONS

International Search Report and Written Opinion, Application No. PCT/US2021/060148, mailed Mar. 17, 2022, 17 pages.
European Search Report and Written Opinion, Application No. EP02768908, dated Apr. 30, 2010.
International Search Report and Written Opinion, Application No. PCT/US2019/042233, mailed Jan. 3, 2020, 17 pages.

* cited by examiner

400

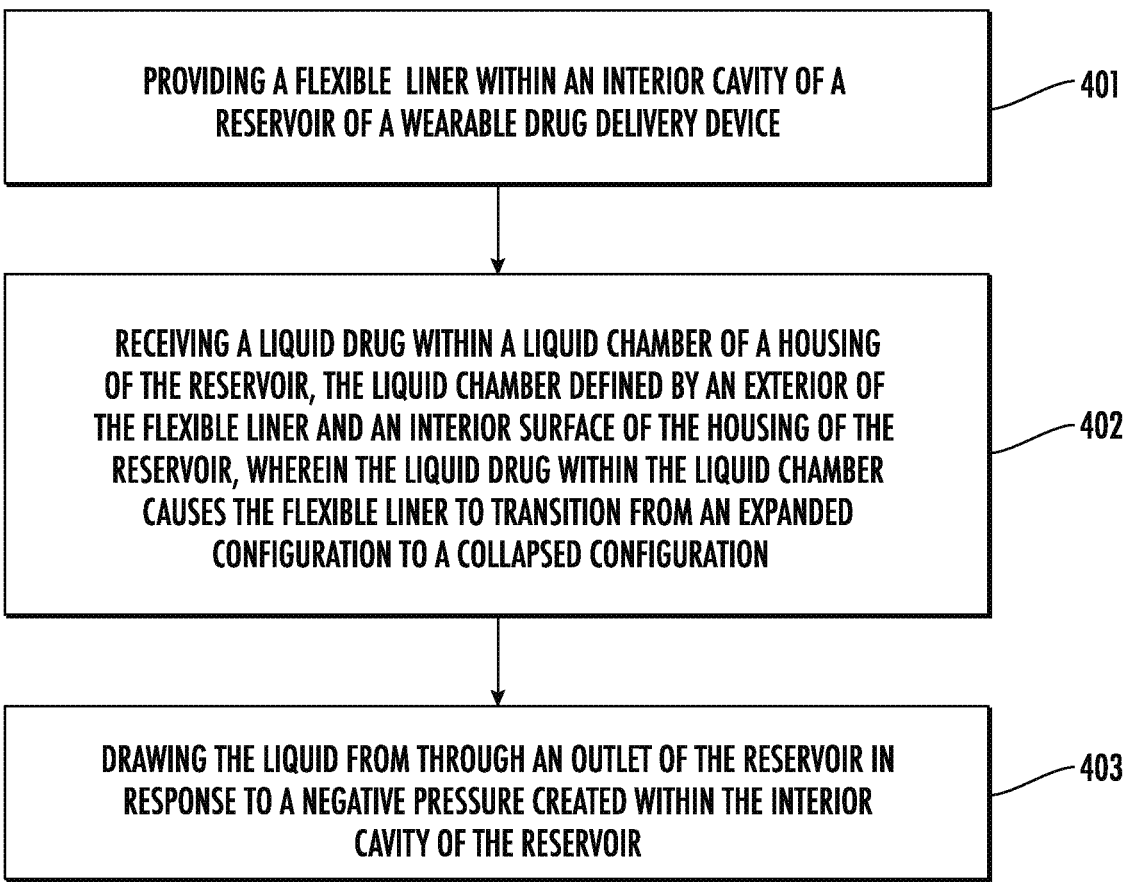

PROVIDING A FLEXIBLE LINER WITHIN AN INTERIOR CAVITY OF A RESERVOIR OF A WEARABLE DRUG DELIVERY DEVICE — 401

RECEIVING A LIQUID DRUG WITHIN A LIQUID CHAMBER OF A HOUSING OF THE RESERVOIR, THE LIQUID CHAMBER DEFINED BY AN EXTERIOR OF THE FLEXIBLE LINER AND AN INTERIOR SURFACE OF THE HOUSING OF THE RESERVOIR, WHEREIN THE LIQUID DRUG WITHIN THE LIQUID CHAMBER CAUSES THE FLEXIBLE LINER TO TRANSITION FROM AN EXPANDED CONFIGURATION TO A COLLAPSED CONFIGURATION — 402

DRAWING THE LIQUID FROM THROUGH AN OUTLET OF THE RESERVOIR IN RESPONSE TO A NEGATIVE PRESSURE CREATED WITHIN THE INTERIOR CAVITY OF THE RESERVOIR — 403

FIG. 7

DRUG DELIVERY DEVICE INCLUDING RESERVOIR WITH FLEXIBLE LINING

RELATED APPLICATIONS

This application claims the benefit of U.S. Provisional Patent Application No. 63/120,349, filed Dec. 2, 2020, the contents of which are incorporated herein by reference in their entirety.

TECHNICAL FIELD

The disclosed embodiments generally relate to medication delivery. More particularly, the disclosed embodiments relate to techniques, processes, systems, and pump devices including a liquid drug reservoir with a flexible lining.

BACKGROUND

Many wearable drug delivery devices include a reservoir for storing a liquid drug. A drive mechanism is operated to expel the stored liquid drug from the reservoir, with positive pressure, for delivery to a user. Some conventional drive mechanisms use a plunger to expel the liquid drug from the reservoir. Accordingly, the drive mechanism generally has a length equal to a length of the reservoir. And when the reservoir is filled, these wearable drive mechanisms require a length of the drug delivery devices to be significantly larger, for example, about twice the length of the reservoir when the plunger has yet to traverse the length of the reservoir to expel fluid. Increasing the size of the drug delivery devices to accommodate filled reservoirs or pre-filled cartridges and corresponding drive mechanism components leads to bulky devices that are uncomfortable for the user to wear.

Accordingly, there is a need for a simplified system for accurately expelling a liquid drug from a reservoir, which also reduces drug delivery device size.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some approaches, a wearable drug delivery device may include a pumping mechanism and a reservoir configured to store and deliver a liquid drug to the pumping mechanism. The reservoir may include a housing defining an interior cavity, the housing comprising an inlet and an outlet, and a flexible liner within the interior cavity, the flexible liner operable to transition between a first configuration and a second configuration in response to an amount of the liquid drug present in a liquid chamber, wherein the liquid chamber is defined by an exterior of the flexible liner and an interior surface of the housing.

In some approaches, a reservoir of a wearable drug delivery device may include a housing defining an interior cavity, the housing comprising an inlet and an outlet. The reservoir may further include a flexible liner within the interior cavity, the flexible liner operable to transition between an expanded configuration and a collapsed configuration in response to an amount of the liquid drug present in a liquid chamber, wherein the liquid chamber is defined by an exterior of the flexible liner and an interior surface of the housing.

Furthermore, in some approaches, a method of operating a reservoir of a wearable drug delivery device may include providing a flexible liner within an interior cavity of a housing of the reservoir and receiving a liquid drug within a liquid chamber of the reservoir. The liquid chamber may be defined by an exterior of the flexible liner and an interior surface of the housing of the reservoir, wherein the liquid drug within the liquid chamber causes the flexible liner to transition from an expanded configuration to a collapsed configuration.

BRIEF DESCRIPTION OF THE DRAWINGS

In the drawings, like reference characters generally refer to the same parts throughout the different views. In the following description, various embodiments of the present disclosure are described with reference to the following drawings, in which:

FIG. 7 illustrates a process flow of a method according to embodiments of the present disclosure.

Figure 1A:
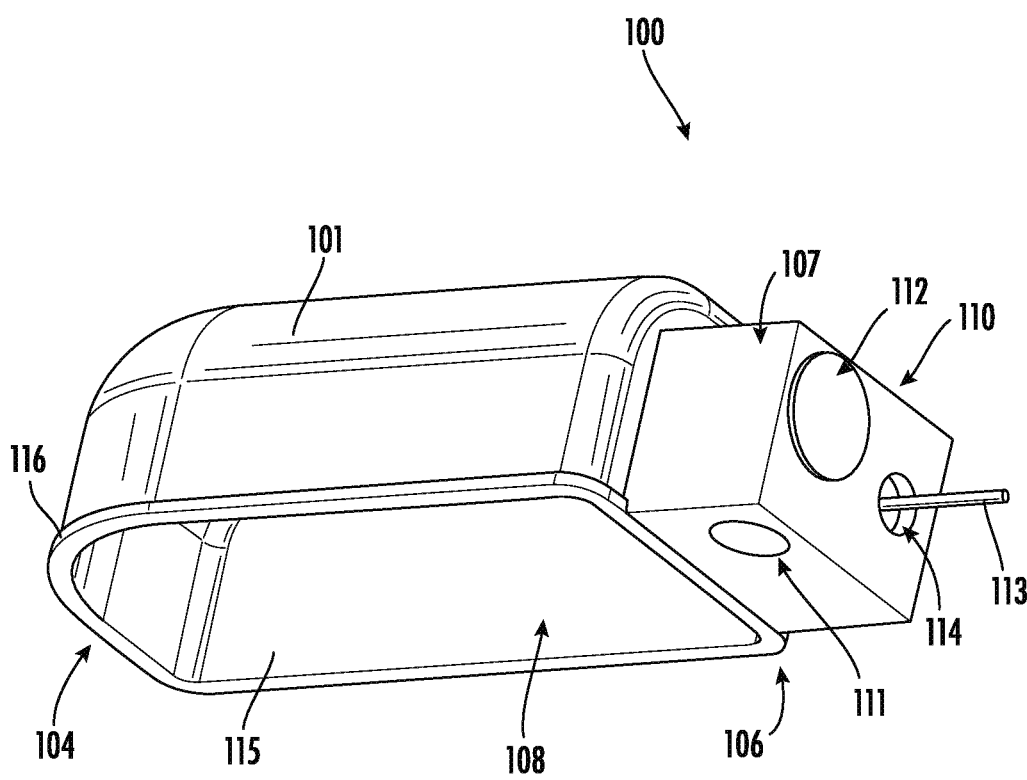
FIG. 1A illustrates a perspective view of a reservoir of a wearable drug delivery device according to embodiments of the present disclosure.

The drawings are not necessarily to scale. The drawings are merely representations, not intended to portray specific parameters of the disclosure. The drawings are intended to depict exemplary embodiments of the disclosure, and therefore are not be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

Embodiments of the present disclosure provide a wearable drug delivery device including a reservoir with a flexible liner within a rigid or semi-rigid housing. An exterior of the flexible liner and an interior surface of the housing may define a liquid chamber. As fluid (e.g., liquid drug) enters the liquid chamber, the flexible liner changes from an expanded natural state to a collapsed state having a reduced volume. As fluid is drawn out of the reservoir, for example, by vacuum pressure, the flexible liner expands back to the original state. In some embodiments, the fluid enters the liquid chamber through a septum connecting the liquid chamber to a fill port chamber, and exits the liquid chamber through an outlet of the housing. The outlet may be connected to a pumping mechanism by an outlet conduit.

The reservoir and flexible liner advantageously allow a more space efficient reservoir, which allows for higher drug capacity, and a smaller pump footprint. Fluid may be drawn from the reservoir using vacuum pressure, as opposed to displacing fluid with positive pressure, which allows for the use of compliant reservoir walls.

In some embodiments, the septum between the fill port chamber and the liquid chamber is a pressure-activated septum including a slit operable to open to fluidly connect the liquid chamber and the fill port chamber. In some embodiments, the fill port chamber may further include a hydrophobic air vent. When the user begins injecting liquid into the fill port chamber from a syringe, the liquid pushes the air from the cavity of the fill port chamber out through the hydrophobic air vent. Once the air is evacuated, the liquid contacts the hydrophobic air vent and is not able to pass through. As the user continues to inject liquid, the pressure builds within the cavity of the fill port chamber. When the fluid pressure surpasses a given threshold, the pressure-activated septum will open to allow the liquid to pass into the liquid chamber of the reservoir. When the pressure build-up diminishes after the fill process is complete, the slit of the pressure-activated septum will close/reseal and once again act as a fluid tight seal. The pressure-activated septum continues to act as a fluid-tight seal during the operation of the wearable drug delivery device.

In some embodiments, the reservoir may include a membrane (e.g., a mesh membrane) in the fluid path between the reservoir and the pump mechanism. During use, as the liquid travels through the membrane, surface tension of any air bubbles in the liquid will attach to the membrane rather than pass through it. The membrane may be, for example, a mesh made of a plastic material with low surface energy. The membrane could also be, for example, a woven metal material or a porous material, such as a foam.

The pressure-activated septum, hydrophobic air vent, and membrane advantageously reduce the chances of air bubbles within the reservoir from passing into the pump mechanism. If this air is not removed, there can be both clinical implications and implications to the operation of the pump mechanism. The clinical implication is that the user may receive air in place of insulin and hence would not be receiving his/her correct therapy dose. In a reciprocating pump, the air bubble could get trapped in such a way that every minimum dose increment is decreased due to the air bubble. Since air is a compressible fluid, if the air bubble is large enough, it could hinder operation of the pump such that the user receives no therapy at all. The membrane is initially permeable to both air and water. As such, if there is tubing or needle length between the reservoir and the membrane, the air initially filling this portion of the fluid path can pass through the membrane when priming the system.

Although non-limiting, embodiments of the present disclosure may further include a delivery pump device operable with the reservoir to draw the fluid therefrom using, e.g., negative pressure. Many different types of delivery pumps may be used with the disclosed liquid drug reservoir, but in one example, the delivery pump device may include an integral shape memory alloy (SMA) wire and resilient sealing member to draw in and expel a fixed volume of fluid (e.g., liquid drug) from a chamber. In some embodiments, the chamber includes an inlet and an outlet, each including a check valve to enable one-way flow into or out of the chamber. Upon activation/contraction of the SMA wire, the resilient sealing member is translated upward within the chamber, compressing the volume and increasing internal chamber pressure. The increased positive pressure eventually opens the outlet valve to deliver the volume of fluid to a cannula or microneedle array. The fixed volume may be a function of internal chamber geometries and SMA stroke. Once the SMA wire fully contracts, the resilient sealing member will be in a compressed state.

When the SMA wire is deactivated, the SMA wire will start to relax and the stored energy of the resilient sealing member will cause the resilient sealing member to spring back to an original position. This motion of the resilient sealing member creates a negative pressure differential in the chamber, thus causing the inlet check valve to open, and drawing fluid back into the chamber. The cycle is then repeated by activating the SMA wire. Advantageously, the delivery pump device of the present disclosure enables a fixed volume of fluid to be delivered and refilled without any secondary steps or additional components. Said another way, the system design and material properties of the SMA wire dictate the fluid response into and out of the chamber.

Figure 1B:
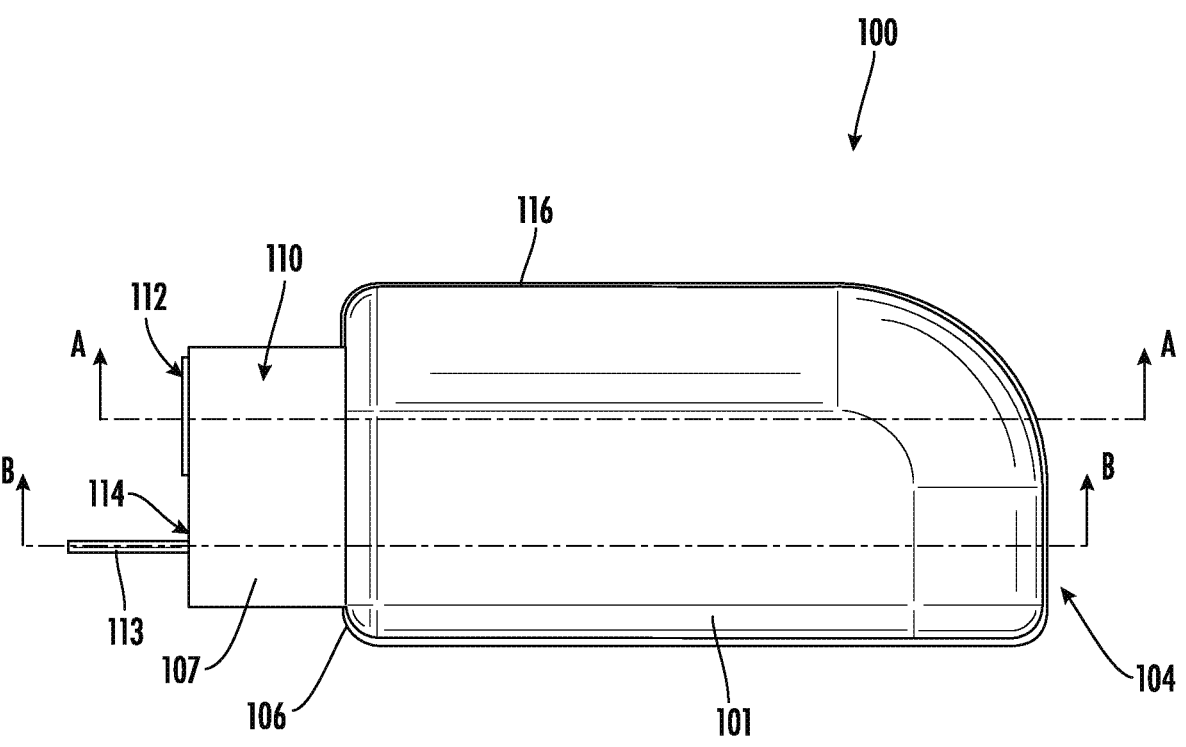
FIG. 1B is a plan view of the reservoir of the wearable drug delivery device according to embodiments of the present disclosure.

FIGS. 1A-1B illustrates a reservoir 100 of a wearable drug delivery device according to embodiments of the present disclosure. The reservoir 100 is operable to store and deliver a liquid to a pumping mechanism of the wearable drug delivery device. As shown, the reservoir 100 may include a housing 101 having a first end 104 opposite a second end 106, and an interior cavity 108. The second end 106 of the reservoir 100 includes an inlet/outlet housing 107 having a fill port chamber 110 including a fill needle inlet 111 and an air vent 112. The inlet/outlet housing 107 may further include an outlet conduit 113 extending through an outlet opening 114. A flexible liner 115 may be located within the interior cavity 108. In some embodiments, the flexible liner 115 may be secured or attached to a frame 116 of the housing 101. As will be described in greater detail herein, the flexible liner 115 is operable to transition between a first configuration (e.g., expanded) and a second configuration (e.g., collapsed) in response to an amount of liquid drug present within the interior cavity 108. In some embodiments, the flexible liner 115 may be made from a shape memory polymer, such as a polymeric smart material, which has the ability to return from a temporary deformed/compressed shape to a permanent shape.

Figure 2A:
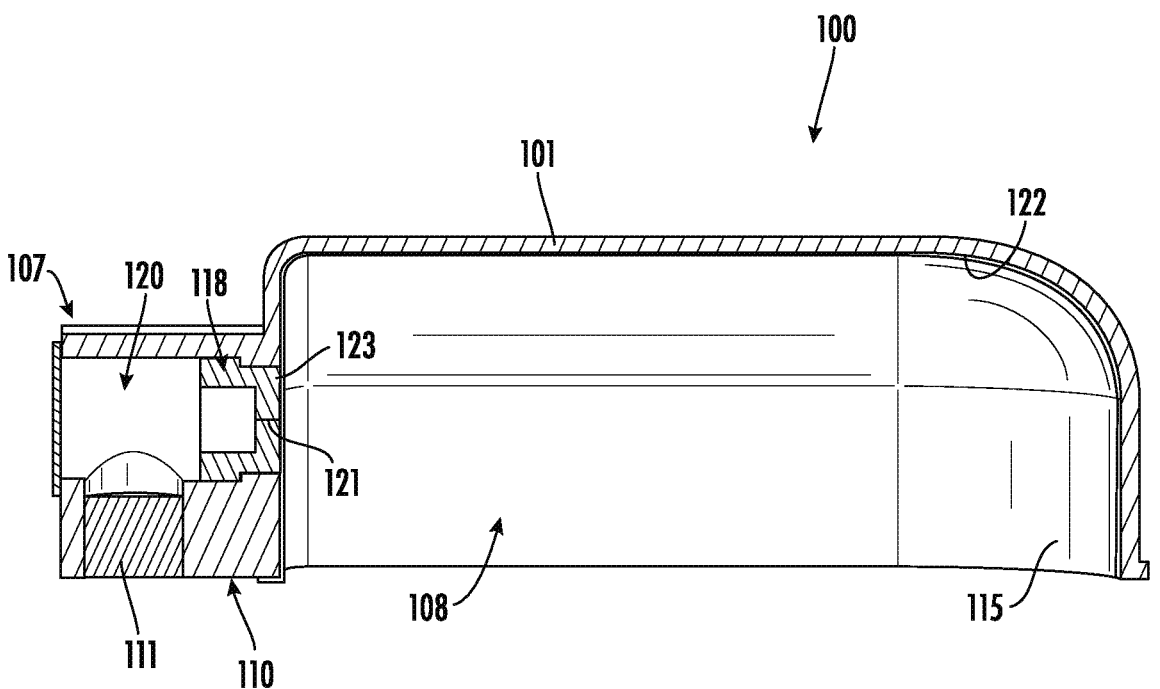
FIGS. 2A-2B are side cross-sectional views, along cutline A-A in FIG. 1B, of the reservoir of the wearable drug delivery device according to embodiments of the present disclosure.
Figure 2B:
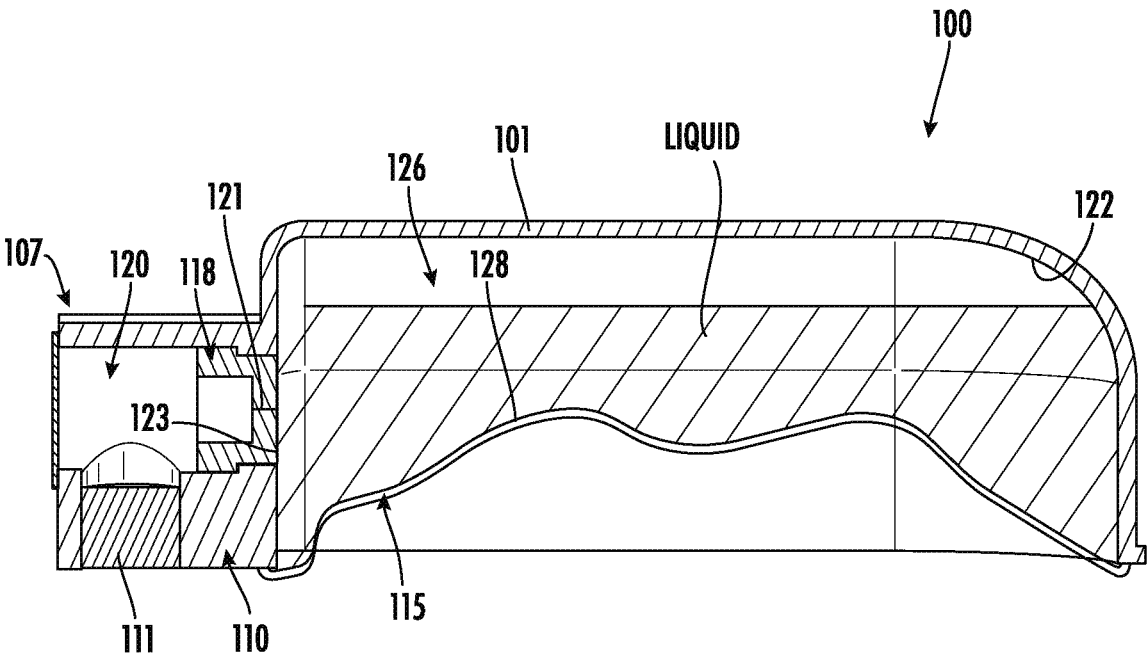

FIGS. 2A-2B are side cross-sectional views, along cutline A-A in FIG. 1B, of the reservoir 100 according to embodiments of the present disclosure. As shown, the reservoir 100 may further include a pressure-activated septum 118 connecting a cavity 120 of the fill port chamber 110 of the inlet/outlet housing 107 and the interior cavity 108 of the housing 101. The pressure-activated septum 118 may include a slit 121 operable to open and close based on a pressure level within the cavity 120 of the fill port chamber 110.

As shown in FIG. 2A, at an initial stage, the flexible liner 115 may be in a natural, expanded configuration in which the flexible liner 115 is positioned against, or directly adjacent, an interior surface 122 of the housing 101. In some embodiments, the flexible liner 115 may initially be flush against an end surface 123 of the pressure-activated septum 118. A liquid drug, medicine, or medicament, such as insulin, may then be injected into the cavity 120 of the fill port chamber 110 via the fill needle inlet 111. When pressure from the liquid drug surpasses a given threshold, the pressure-activated septum 118 will open to allow the liquid to pass into a liquid chamber 126 of the reservoir 100, as shown in FIG. 2B. The liquid chamber 126 may be defined by an exterior 128 of the flexible liner 115 and the interior surface 122 of the housing 101. Unlike conventional approaches in which the liquid fills and expands the liner, embodiments herein provide the liquid along the exterior 128 to decrease a volume of the flexible liner 115 as more liquid enters the liquid chamber 126. As shown, the flexible liner 115 is configured to buckle, collapse, and/or fold under the liquid.

Figure 2C:
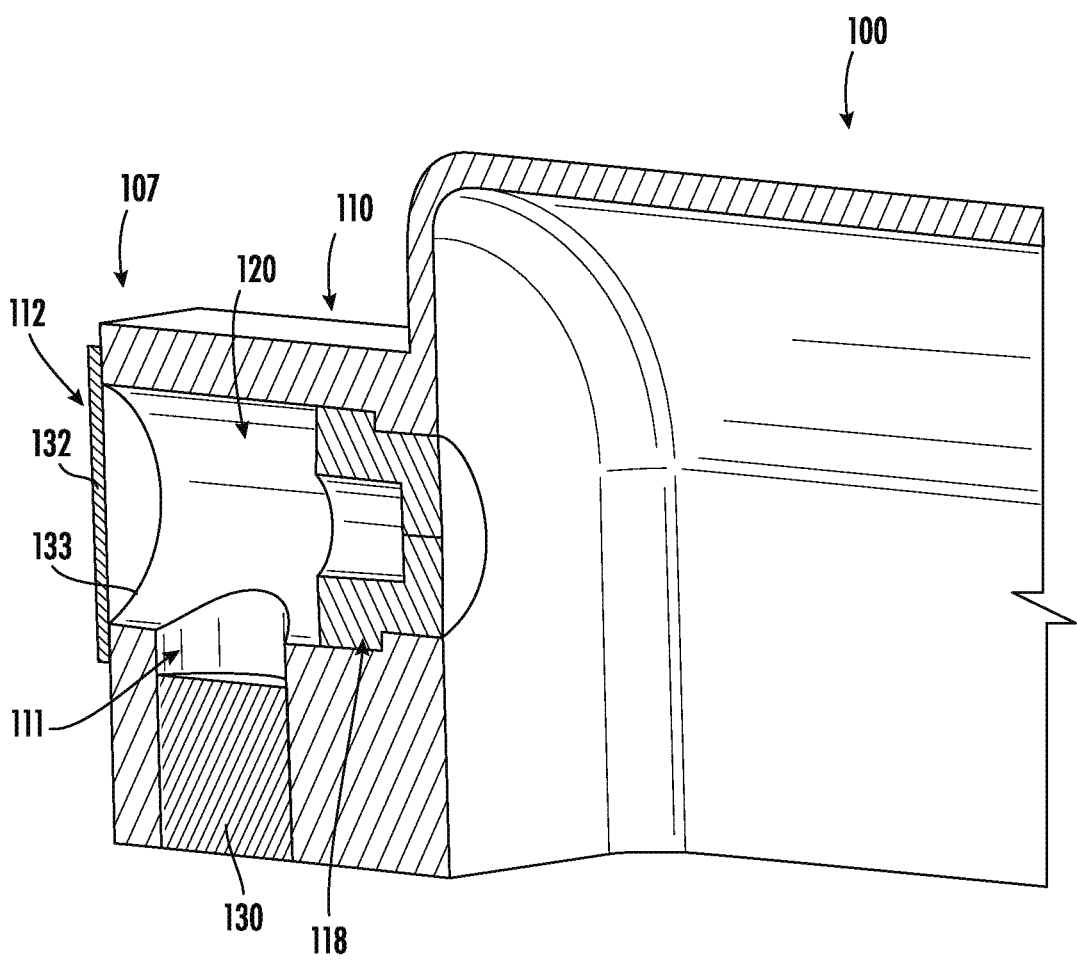
FIG. 2C is a perspective cross-sectional view of a fill port chamber of the reservoir of the wearable drug delivery device according to embodiments of the present disclosure.

FIG. 2C is a perspective cross-sectional view of the fill port chamber 110 in greater detail. As shown, the fill port chamber 110 may include the fill needle inlet 111 having a self-sealing septum 130 provided therein. A needle/syringe (not shown) may be inserted through the self-sealing septum 130 to inject the liquid into the cavity 120 of the fill port chamber 110. Although non-limiting, the self-sealing septum 130 may be constructed from any material capable of re-forming a liquid-tight seal after the needle/syringe is removed from the fill needle inlet 111.

As further shown, the fill port chamber 110 includes the air vent 112 at one end of the cavity 120. In some embodiments, the air vent 112 includes a hydrophobic cover 132 extending across an air vent opening 133. When the user begins injecting the liquid into the cavity 120, the liquid pushes air from the cavity 120 out through the air vent 112. Once the air is evacuated, the liquid contacts the hydrophobic cover 132 and is not able to pass therethrough.

Figure 3A:
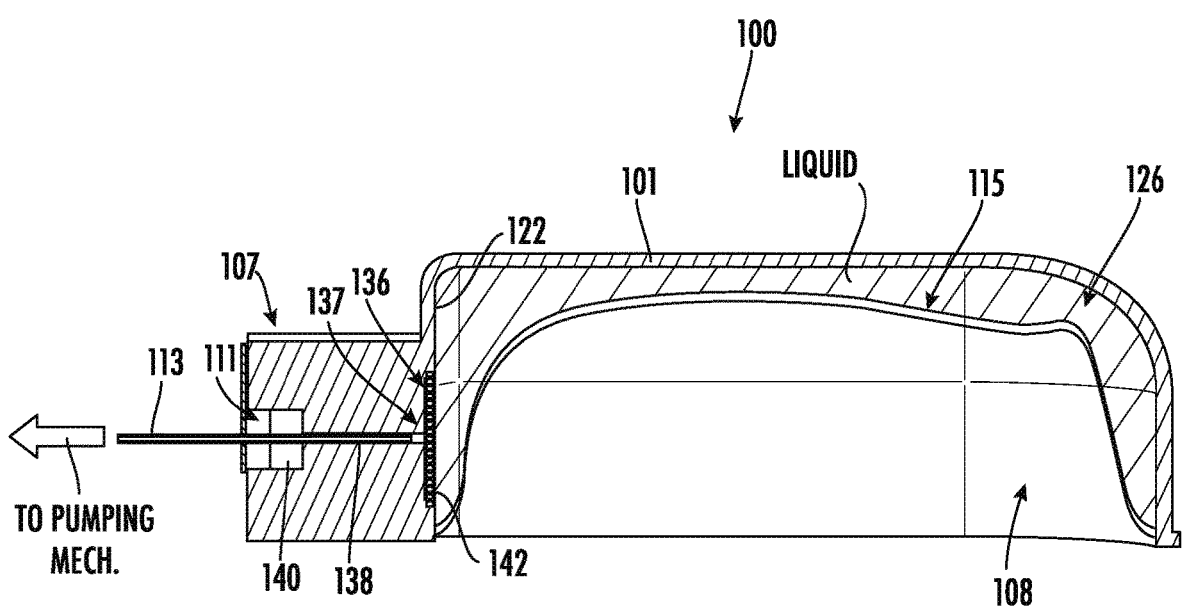
FIG. 3A is a side cross-sectional view, along cutline B-B in FIG. 1B, of the reservoir of the wearable drug delivery device according to embodiments of the present disclosure.
Figure 3B:
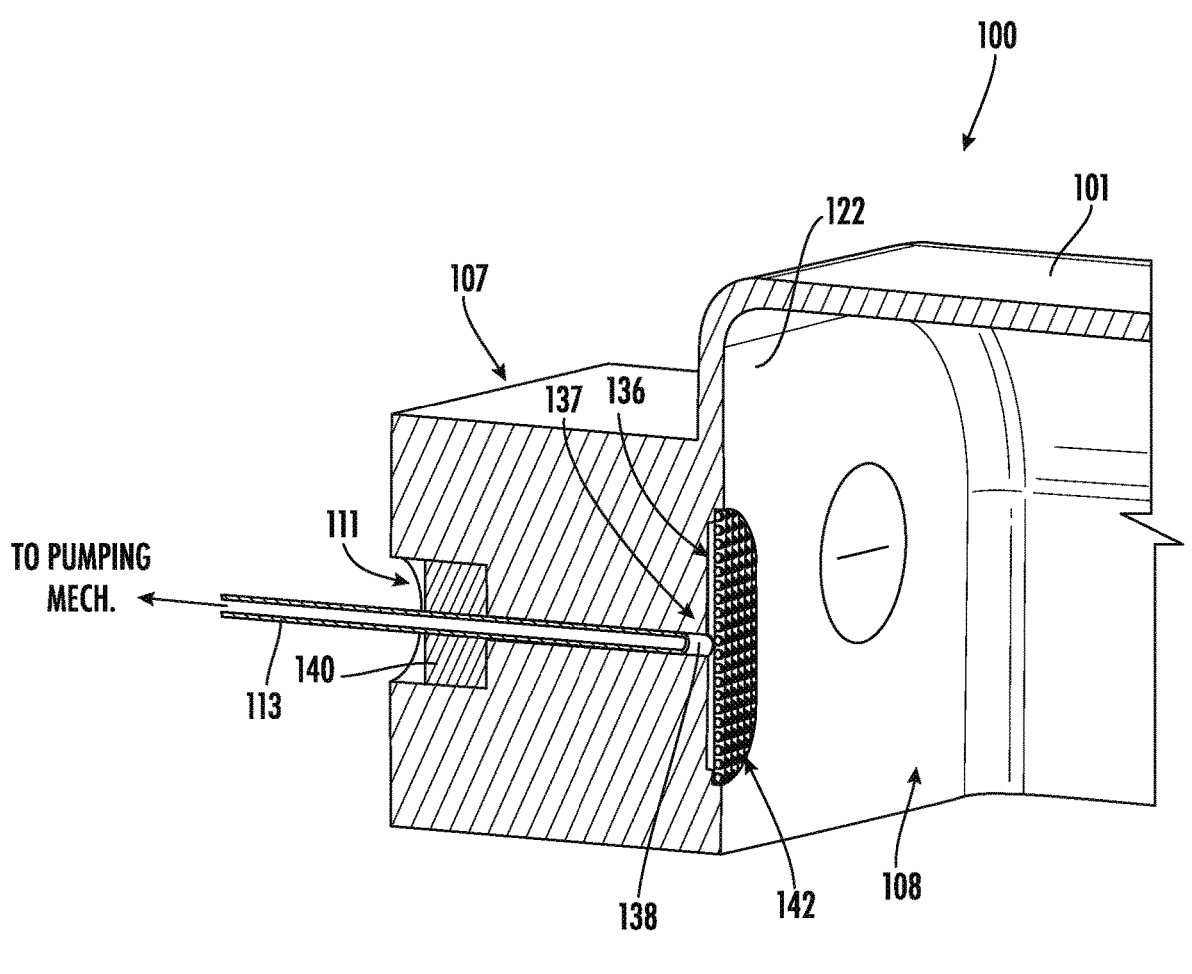
FIG. 3B is a perspective cross-sectional view of an inlet/outlet housing of the reservoir of the wearable drug delivery device according to embodiments of the present disclosure.

FIGS. 3A-3B demonstrate an outlet 137 of the reservoir 100 according to embodiments of the present disclosure. FIG. 3A is a side cross-sectional view, along cutline B-B in FIG. 1B, demonstrating the flexible liner 115 in an intermediate configuration in which the flexible liner 115 is transitioning between a collapsed state to a more expanded state, e.g., in response to a negative pressure within the interior cavity 108. In some embodiments, the outlet 137 may include an outlet cavity 136 recessed into the interior surface 122 of the housing 101. The outlet cavity 136 may be connected with an outlet path 138 in which the outlet conduit 113 is provided. In some embodiments, the outlet path 138 is plugged by a fluid seal element 140, which may also secure the conduit 113 in place.

As further shown, a membrane 142 may extend across the outlet cavity 136. The membrane 142 may initially be permeable to both air and water. Eventually, the liquid will travel through openings of the membrane 142, while the air becomes trapped. Although non-limiting, the membrane 142 may be a mesh made of a plastic material with low surface energy. In other embodiments, the membrane 142 could also be a woven metal material or a porous material, such as a foam.

Figure 4A:
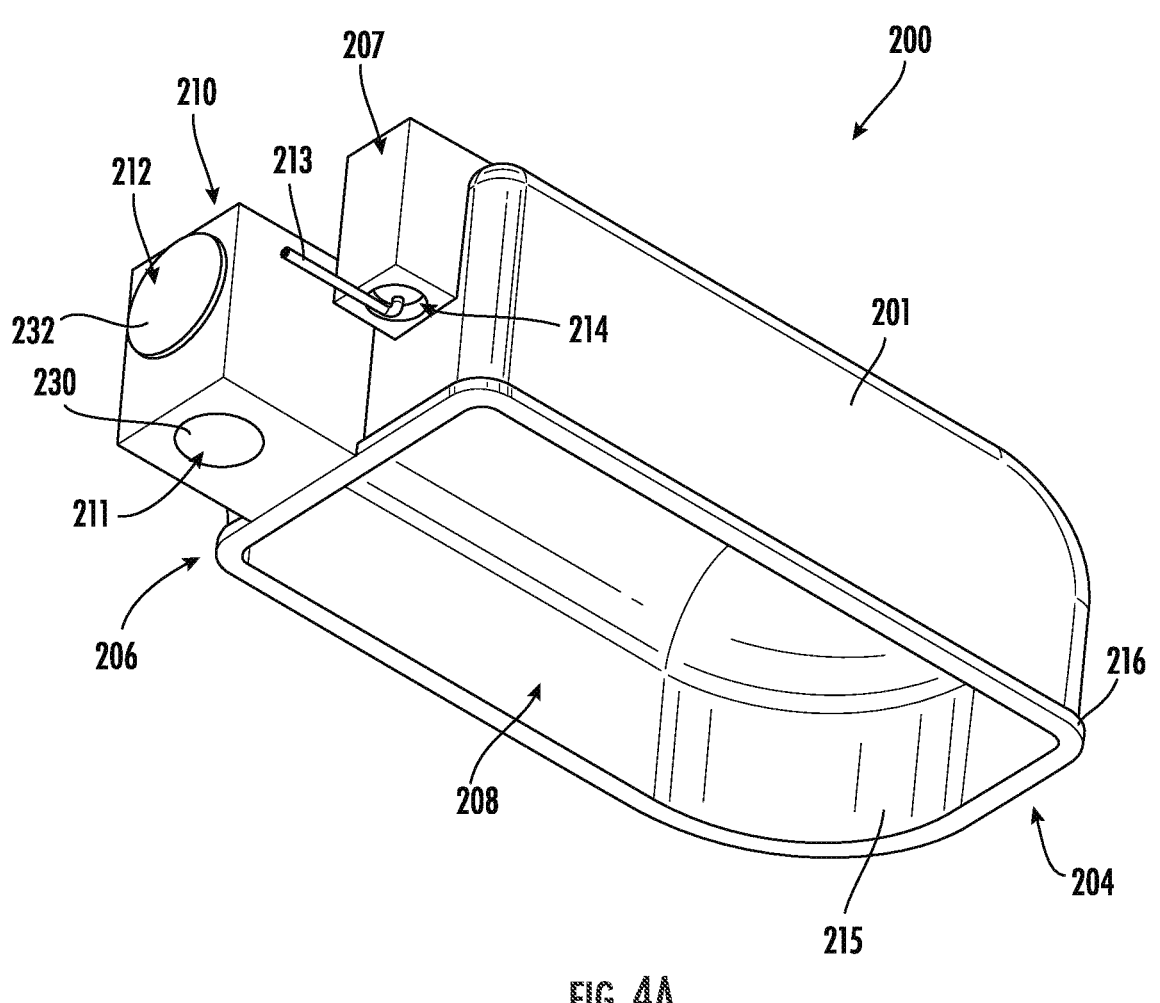
FIG. 4A illustrates a perspective view of a reservoir of a wearable drug delivery device according to embodiments of the present disclosure.
Figure 4B:
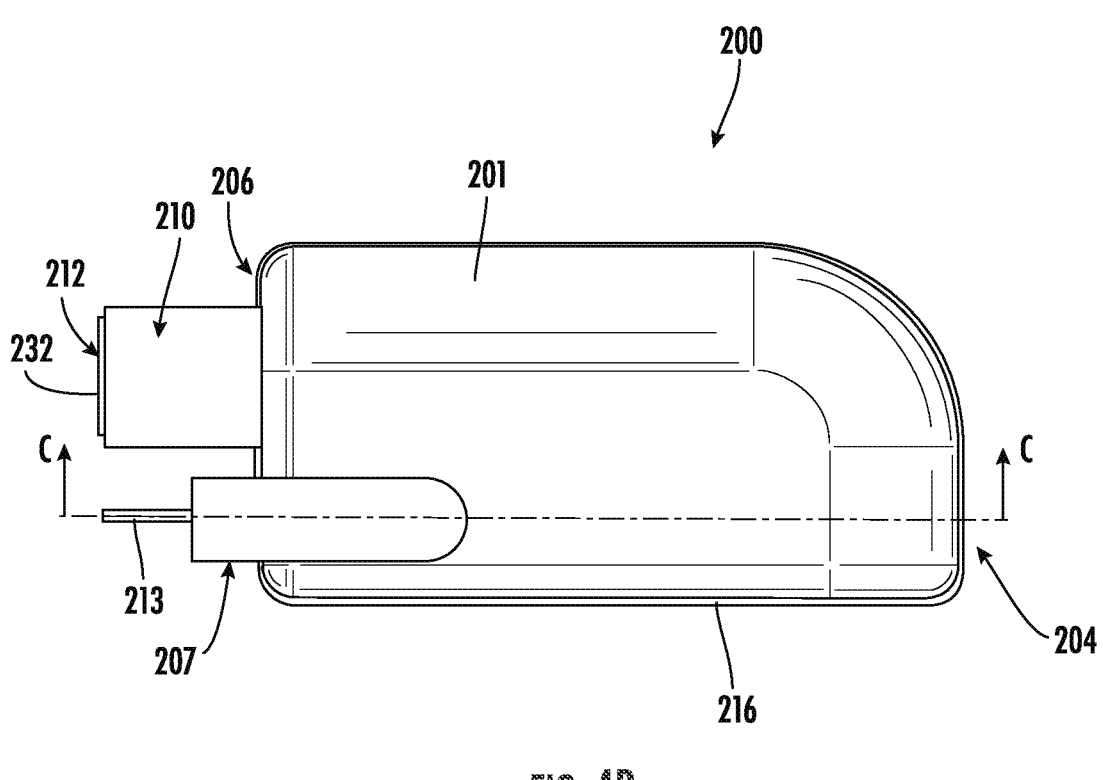
FIG. 4B is a plan view of the reservoir of the wearable drug delivery device according to embodiments of the present disclosure.

FIGS. 4A-4B illustrate a reservoir 200 of a wearable drug delivery device according to embodiments of the present disclosure. The reservoir 200 may be similar in many aspects to the reservoir 100 described herein. As such, only certain features of the reservoir 200 will hereinafter be described for the sake of brevity. As shown, the reservoir 200 may include a housing 201 having a first end 204 opposite a second end 206, and an interior cavity 208. At the second end 206 of the reservoir 200 is a fill port chamber 210 and an outlet housing 207. The fill port chamber 210 may include a fill needle inlet 211 and an air vent 212. The outlet housing 207 may include an outlet conduit 213 extending through an outlet opening 214. A flexible liner 215 may be located within the interior cavity 208 and secured to a frame 216 of the housing 201.

Although not shown, the reservoir 200 may further include a pressure-activated septum (similar to the pressure-activated septum 118 described above), connecting a cavity of the fill port chamber 210 of the inlet/outlet housing 207 and the interior cavity 208 of the housing 201. The pressure-activated septum may include a slit operable to open and close based on a pressure level within the cavity of the fill port chamber 210.

During use, a liquid drug, medicine, or medicament, such as insulin, may be injected into the cavity of the fill port chamber 210 via the fill needle inlet 211. The flexible liner 215 may transition between a natural, expanded configuration in which the flexible liner 215 is positioned against, or directly adjacent, an interior surface of the housing 201, as shown in FIG. 4A. In some embodiments, the flexible liner 215 may initially be flush against the pressure-activated septum. When pressure from the liquid drug surpasses a given threshold, the pressure-activated septum will open to allow the liquid to pass into a liquid chamber of the reservoir 200. The liquid chamber may be defined as an area within the housing 101 between an exterior of the flexible liner 215 and the interior surface of the housing 101. As described above, the flexible liner 215 is configured to buckle, collapse, and/or fold under the liquid as the volume of liquid within the liquid chamber increases.

In some embodiments, the fill port chamber 210 may include the fill needle inlet 211 having a self-sealing septum 230 provided therein. A needle/syringe (not shown) may be inserted through the self-sealing septum 230 to inject the liquid into the cavity of the fill port chamber 210. Although non-limiting, the self-sealing septum 230 may be constructed from any material capable of re-forming a liquid-tight seal after the needle/syringe is removed from the fill needle inlet 211.

As further shown, the fill port chamber 210 includes the air vent 212 at one end of the cavity 220. In some embodiments, the air vent 212 includes a hydrophobic cover 232 extending across an air vent opening. When the user begins injecting the liquid into the cavity, the liquid pushes air from the cavity out through the air vent 212. Once the air is evacuated, the liquid contacts the hydrophobic cover 232 and is not able to pass therethrough.

Figure 5A:
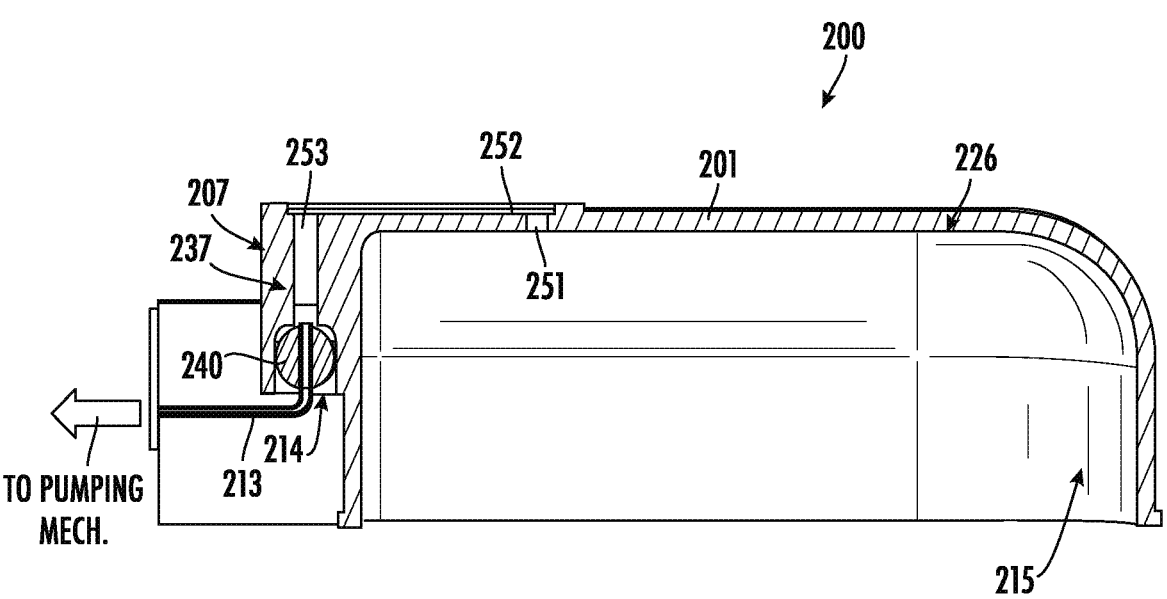
FIG. 5A is a side cross-sectional view, along cutline C-C in FIG. 4B, of the reservoir of the wearable drug delivery device according to embodiments of the present disclosure.
Figure 5B:
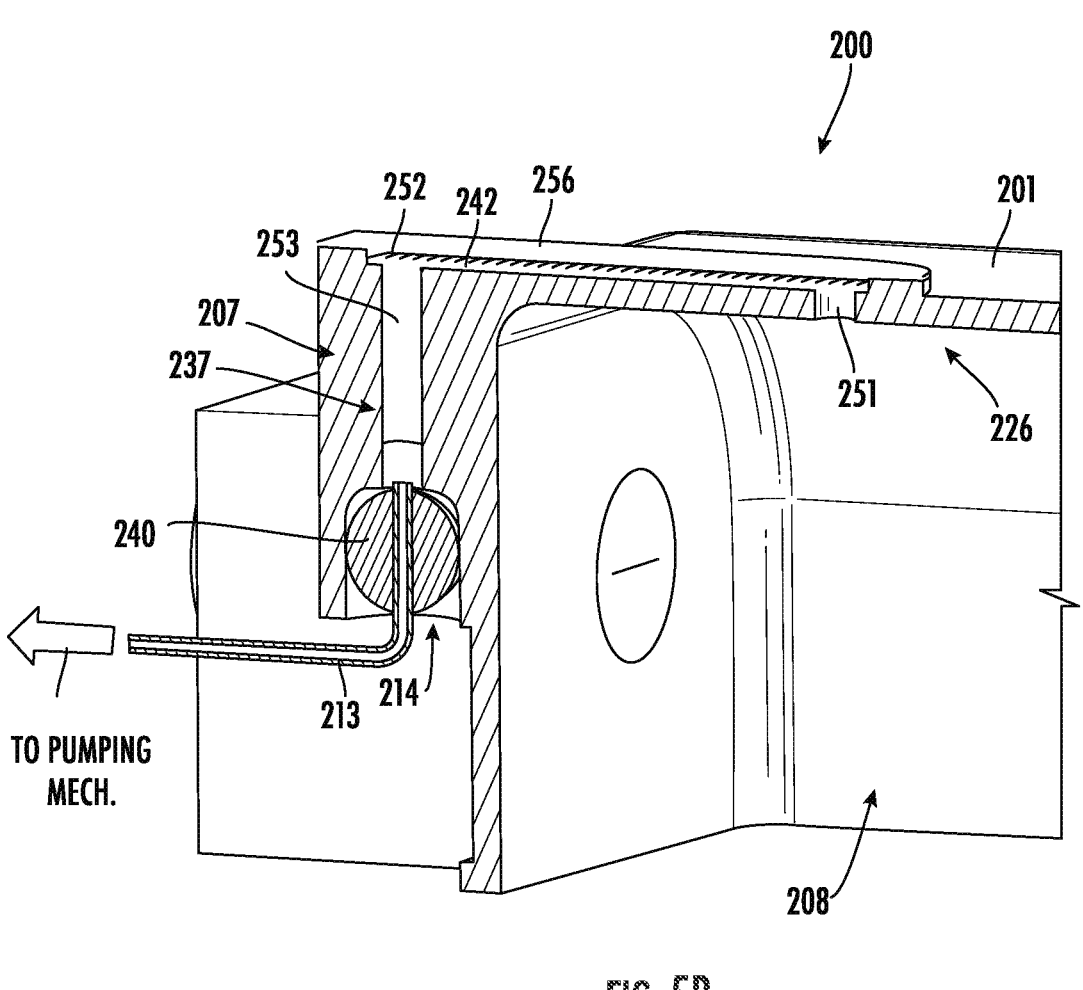
FIG. 5B is a perspective cross-sectional view of an inlet/outlet housing of the reservoir of the wearable drug delivery device according to embodiments of the present disclosure.

FIGS. 5A-5B demonstrate an outlet 237 of the reservoir 200 according to embodiments of the present disclosure. FIG. 5A is a side cross-sectional view, along cutline C-C in FIG. 4B, while FIG. 5B is perspective cross-sectional view of the outlet housing 207 in greater detail. The liner 215 is not present in FIG. 5B. In some embodiments, the outlet 237 may include a first outlet path 251 extending between liquid chamber 226 and an outlet chamber 252. In some embodiments, the outlet chamber 252 may be fluidly connected with a second outlet path 253 and the outlet opening 214. As shown, the outlet conduit 213 may extend partially into the second outlet path 253. In some embodiments, the second outlet path 253 and the outlet opening 214 are plugged or blocked by a fluid seal element 240.

As better demonstrated in FIG. 5B, a membrane 242 may be positioned within the outlet chamber 252. The outlet housing 207 may include a removable membrane cover 256 (e.g., plastic film) to permit access to the membrane 242 within the outlet chamber 252. As shown, the membrane 242 may extend across both the first outlet path 251 and the second outlet path 253. During use, the liquid will travel through the first outlet path 251 and the membrane 242, and enter the outlet chamber 252. The liquid may then pass through the membrane 242 a second time as the liquid enters the second outlet path 253 from the outlet chamber 252. Although non-limiting, the membrane 242 may be a mesh made of a plastic material with low surface energy. In other embodiments, the membrane 242 could also be a woven metal material or a porous material, such as a foam.

Figure 6A:
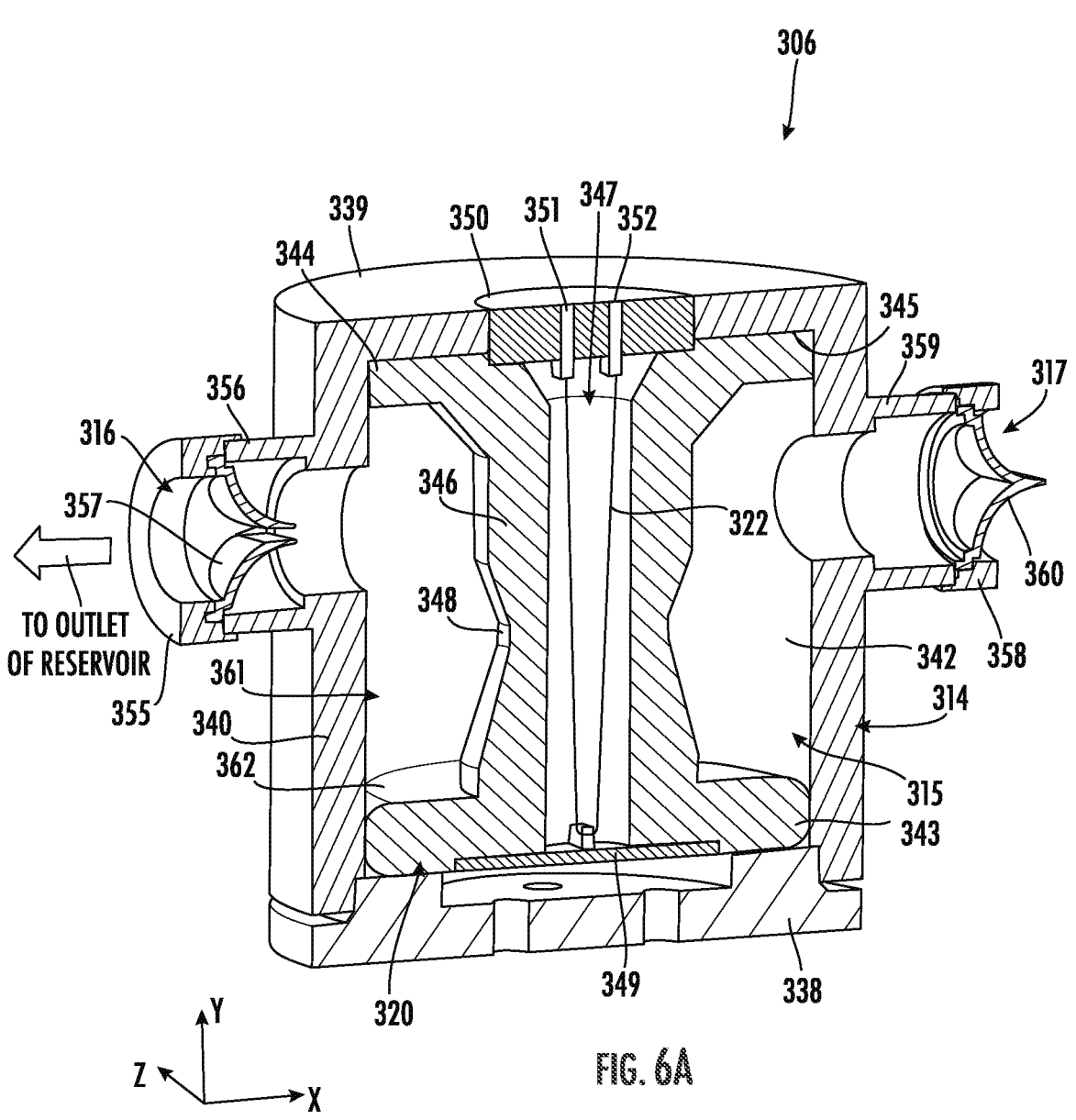
FIGS. 6A-6B illustrate perspective cross-sectional views of a drive mechanism of a delivery pump device according to embodiments of the present disclosure.
Figure 6B:
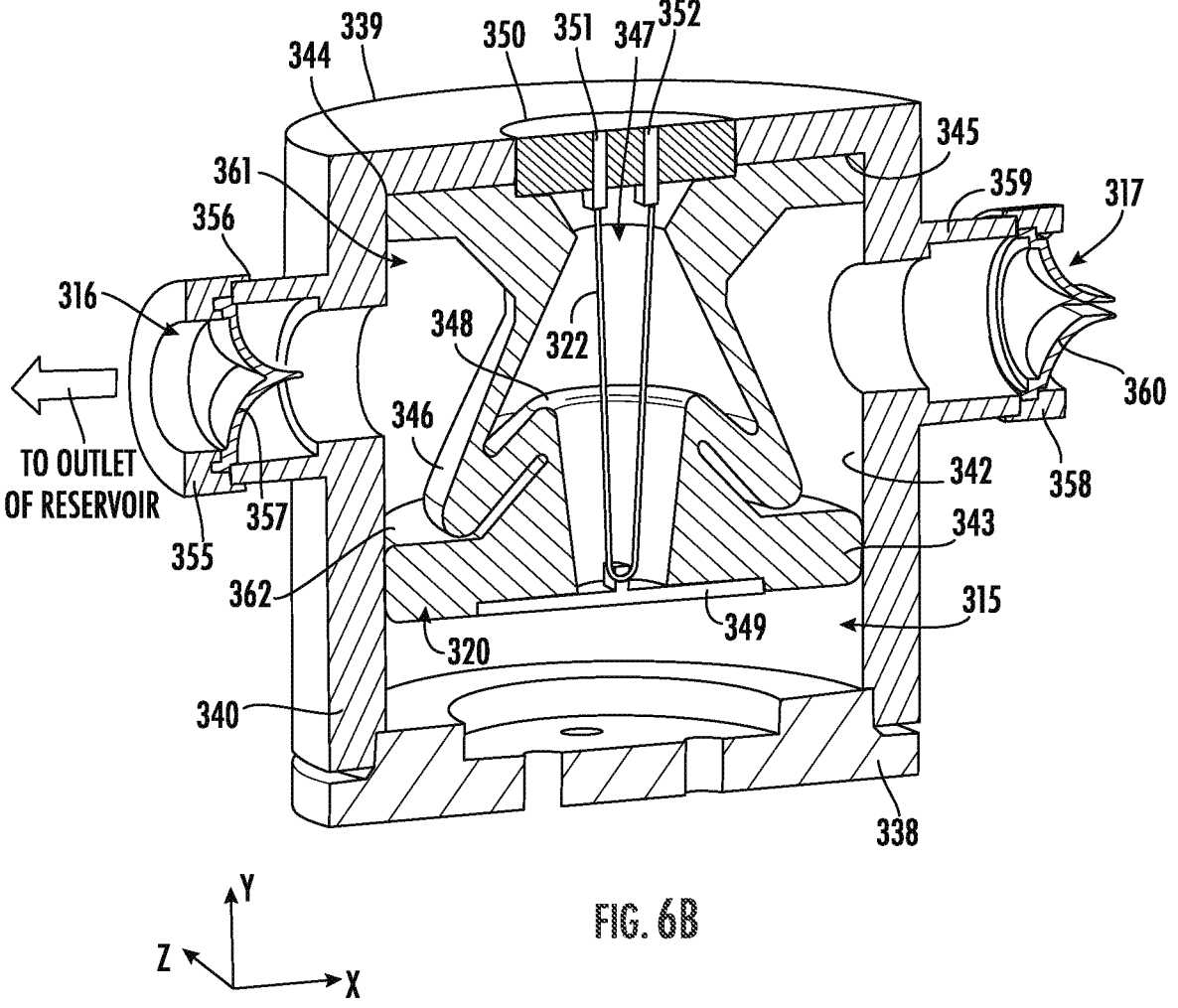

Turning now to FIGS. 6A-6B, a non-limiting approach for creating negative pressure within the reservoir 100/200 to draw the liquid therefrom will be described. In some embodiments, the wearable drug delivery device may include a drive mechanism 306 connected to the reservoir 100/200. As shown, the drive mechanism 306 may include a housing 314 defining a chamber 315. The housing 314 may include a bottom wall 338 opposite a top wall 339, and a sidewall 340 extending between the bottom wall 338 and the top wall 339. An interior surface 342 of the sidewall 340 may partially define the chamber 315. Although shown generally as cylindrically shaped, the sidewall 340, the bottom wall 338, and/or the top wall 339 may take on a different configuration in alternative embodiments.

As further shown, the drive mechanism 306 includes the resilient sealing member 320 within the chamber 315. The resilient sealing member 320 may include a first flange 343 in direct contact with the interior surface 342 of the sidewall 340 to form a seal therebetween. The resilient sealing member 320 may further include a second flange 344 fixed to an underside 345 of the top wall 339 and/or the interior surface 342 of the sidewall 340. During use, the second flange 344 is generally stationary, while the first flange 343 is permitted to move between the bottom wall 338 and the top wall 339, e.g., along the y-direction. The resilient sealing member 320 may further include a central section 346 extending between the first and second flanges 343, 344. In some embodiments, the central section 346 may have a varied thickness, e.g., along the x-direction and/or the z-direction. Specifically, the central section 346 may include one or more weakened areas 348 to promote folding or collapsing of the resilient sealing member 320 as the first flange 343 is brought towards the second flange 344. In other embodiments, the central section 346 may have a substantially constant thickness.

Although non-limiting, the resilient sealing member 320 may be made from a shape memory polymer, such as a polymeric smart material, which has the ability to return from a temporary deformed/compressed shape to a permanent shape. For example, the configuration of the resilient sealing member 320 in FIG. 6A may correspond to its natural or permanent shape, while the configuration of the resilient sealing member 320 in FIG. 6B may correspond to the temporary deformed/compressed shape.

An SMA wire 322 of the drive mechanism 306 may extend through a channel 347 of the resilient sealing member 320. As shown, the SMA wire 322 may be connected with a base plate 349, which may be in contact (e.g., beneath) the resilient sealing member 320 to bias the resilient sealing member 320 between a first position, such as the position demonstrated in FIG. 6A, and a second position, such as the position demonstrated in FIG. 6B. The base plate 349 may provide support and rigidity to the first flange 343 of the resilient sealing member 320. In some embodiments, the base plate 349 is fixed to the first flange 343.

The SMA wire 322 can be coupled to a power element (not shown) by way of a contact 350, a first pole or connector 351, and a second pole or connector 352. The power element can be used to energize both legs/sides of the SMA wire 322, as further described herein. The first connector 351 may be coupled to a first output of the power element (e.g., a positive output terminal), and the second connector 352 can be coupled to a second output of the power element 332 (e.g., a negative output terminal). The contact 350 can be connected to ground or a ground terminal.

During use, the power element may be activated to energize the SMA wire 322, which causes the SMA wire 322 to change shape (e.g., contract). More specifically, the activated SMA wire 322 begins to shorten (e.g., along the y-direction), after having previously been passively relaxed, pulling the base plate 349 and the first flange 343 towards the top wall 339 of the housing 314, as the SMA wire 322 strives to return to its memorized or natural/pre-stressed shape and length. In various embodiments, contraction of the SMA wire 322 may be controlled by increasing or decreasing heat generated by the power element 332. For example, a lower current supplied to the SMA wire 322 may cause the base plate 349 to move more slowly than a higher current.

The drive mechanism 306 may further include an inlet port 316 and an outlet port 317. In some embodiments, the inlet port 316 is fluidly connected to the outlet conduit 113/213 of the reservoir 100/200. As shown, the inlet port 316 may include an inlet cap 355 coupled to an inlet cylinder 356. An inlet valve 357, such as a check valve or one-way valve, may be positioned within the inlet cylinder 356. Similarly, the outlet port 317 may include an outlet cap 358 coupled to an outlet cylinder 359. An outlet valve 360, which may also be a check valve or one-way valve, is positioned within the outlet cylinder 359. The inlet valve 357 is configured to permit the liquid drug to only flow into the chamber 315, while the outlet valve 360 is configured to permit the liquid drug to only flow out of the chamber 315.

When the inlet valve 357 is opened, as shown in FIG. 6A, the liquid drug flows from the reservoir 100/200, through the outlet conduit 113/213 and the inlet cylinder 356, and into a liquid chamber 361, which may be an area of the chamber 315 defined by an outer surface 362 of the resilient sealing member 320 and the interior surface 342 of the housing 314. A volume of the liquid chamber 361 may change as the resilient sealing member 320 changes configuration. For example, as the resilient sealing member 320 moves towards the top wall 339 of the housing 314, the volume of the liquid chamber 361 decreases, which increases pressure within the housing, causing the outlet valve 360 to open, as shown in FIG. 6B. In various embodiments, a length (e.g., along the x-direction) of the inlet cylinder 356 and the outlet cylinder 359 may be the same or different. Furthermore, an inner diameter of the inlet cylinder 356 and the outlet cylinder 359 may be the same or different.

FIG. 7 illustrates an example process 400 according to embodiments of the present disclosure. At block 401, the process 400 may include providing a flexible liner within an interior cavity of a reservoir of a wearable drug delivery device. In some embodiments, the flexible liner may be made from a shape memory polymer, such as a polymeric smart material, which has the ability to return from a temporary deformed/compressed shape to a permanent shape.

At block 402, the process 400 may include receiving a liquid drug within a liquid chamber of a housing of the reservoir, the liquid chamber defined by an exterior of the flexible liner and an interior surface of the housing of the reservoir, wherein the liquid drug within the liquid chamber causes the flexible liner to transition from an expanded configuration to a collapsed configuration.

In some embodiments, the process 400 may further include connecting a fill port chamber to the housing by a pressure-activated septum, and receiving, via a fill needle inlet, the liquid drug into the fill port chamber. A slit of the pressure-activated septum is operable to open in response to increased pressure within the fill port chamber.

At block 403, the process 400 may optionally include drawing the liquid drug through an outlet of the reservoir in response to a negative pressure created within the interior cavity of the reservoir. In some embodiments, the negative pressure is created through operation of a drive mechanism of a pumping mechanism. In some embodiments, process 400 may further include providing a membrane across the outlet of the housing, wherein the liquid drug passes through the membrane before reaching the outlet conduit.

Figure 8:
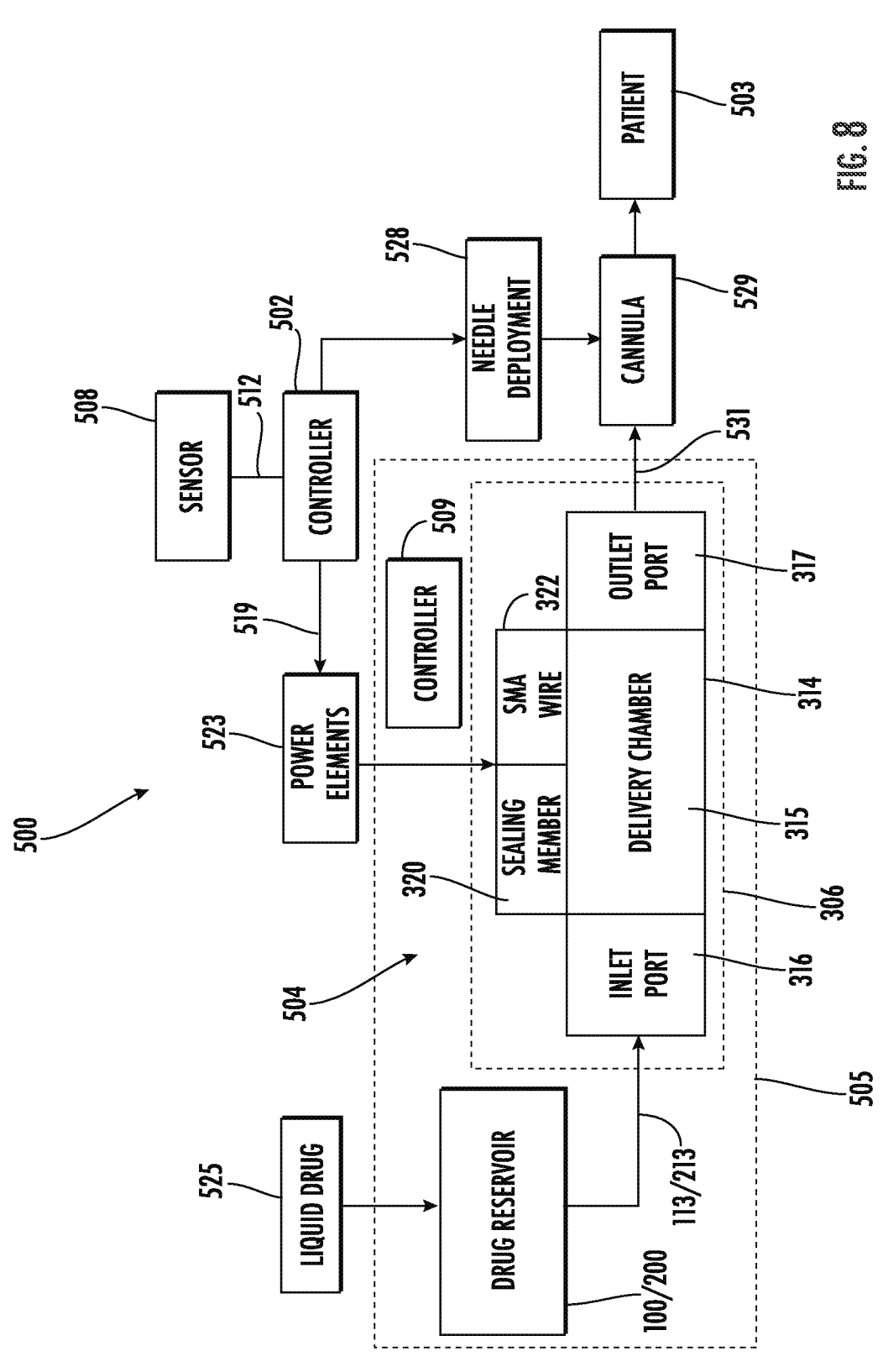
FIG. 8 illustrates a schematic diagram of a drug delivery system according to embodiments of the present disclosure.

FIG. 8 illustrates a simplified block diagram of an example system 500. The system 500 may be a wearable or on-body drug delivery device attached to the skin of a user/patient 503. The system 500 may include a controller 502, a pumping mechanism 504 (hereinafter "pump 504"), and a sensor 508. The sensor 508 may be a glucose or other analyte monitor such as, for example, a continuous glucose monitor. The sensor 508 may, for example, be operable to measure blood glucose (BG) values of a user to generate a measured BG level signal 512. The controller 502, the pump 504, and the sensor 508 may be communicatively coupled to one another via a wired or wireless communication path. For example, each of the controller 502, the pump 504 and the sensor 508 may be equipped with a wireless radio frequency transceiver operable to communicate via one or more communication protocols, such as Bluetooth®, or the like. The system 500 may also include a delivery pump device (hereinafter "device") 505, which includes the drive mechanism 306 having the housing 314 defining the chamber 315, the inlet port 316, and the outlet port 317. The drive mechanism 306 may further include the resilient sealing member 320 within the chamber 315, the resilient sealing member 320 connected to the SMA wire 322. The system 500 may include additional components not shown or described for the sake of brevity.

The controller 502 may receive a desired BG level signal, which may be a first signal, indicating a desired BG level or range for the patient 503. The desired BG level signal may be stored in memory of a controller 509 on device 505, received from a user interface to the controller 502, or another device, or by an algorithm within controller 509 (or controller 502) that automatically determines a BG level for the patient 503. The sensor 508 may be coupled to the patient 503 and operable to measure an approximate value of a BG level of the user. In response to the measured BG level or value, the sensor 508 may generate a signal indicating the measured BG value. As shown in the example, the controller 502 may also receive from the sensor 508 via a communication path, the measured BG level signal 512, which may be a second signal.

Based on the desired BG level signal and the measured BG level signal 512, the controller 502 or controller 509 may generate one or more control signals for directing operation of the pump 504. For example, one control signal 519 from the controller 902 or controller 509 may cause the pump 504 to turn on, or activate one or more power elements 523 operably connected with the device 505. As described above, the power elements 523 may activate the SMA wire 322, causing the SMA wire 322 to change shape and/or length, which in turn will change a configuration of the resilient sealing member 320. The specified amount of a liquid drug 525 (e.g., insulin) may then be drawn into the chamber 315, from the reservoir 100/200, via outlet conduit 113/213, and through the inlet port 316, in response to a change in pressure due to the change in configuration of the resilient sealing member 320. Ideally, the specified amount of the liquid drug 525 may be determined based on a difference between the desired BG level signal and the actual BG signal level 512. The specified amount of the liquid drug 525 may be determined as an appropriate amount of insulin to drive the measured BG level of the user to the desired BG level. Based on operation of the pump 504, as determined by the control signal 519, the patient 503 may receive the liquid drug from the reservoir 100/200. The system 500 may operate as a closed-loop system, an open-loop system, or as a hybrid system. In an exemplary closed-loop system, the controller 509 may direct operation of the device 505 without input from the controller 502, and may receive BG level signal 512 from the sensor 508. The sensor 508 may be housed within the device 505 or may be housed in a separate device and communicate wirelessly directly with the device 505.

As further shown, the system 500 may include a needle deployment component 528 in communication with the controller 502 or the controller 509. The needle deployment component 528 may include a needle/cannula 529 deployable into the patient 503 and may have one or more holes at a distal end thereof. The cannula 529 may form a portion of a fluid path coupling the patient 503 to the reservoir 100/200. More specifically, the inlet port 316 may be coupled to the reservoir 100/200 by the outlet conduit 113/213. The outlet conduit 113/213 may be of any size and shape and may be made from any material. The outlet conduit 113/213 can allow fluid, such as the liquid drug 525 in the reservoir 100/200, to be transferred to the device 505 through the inlet port 316.

As further shown, the outlet port 317 may be coupled to the cannula 529 by a second fluid path component 531. The second fluid path component 531 may be of any size and shape and may be made from any material. The second fluid path component 531 may be connected to the cannula 529 to allow fluid expelled from the device 505 to be provided to the patient 503. The outlet conduit 113/213 and the second fluid path component 531 may be rigid or flexible.

The controller 502/509 may be implemented in hardware, software, or any combination thereof. The controller 502/509 may, for example, be a processor, a logic circuit or a microcontroller coupled to a memory. The controller 502/509 may maintain a date and time as well as other functions (e.g., calculations or the like) performed by processors. The controller 502/509 may be operable to execute an artificial pancreas (AP) algorithm stored in memory (not shown) that enables the controller 502/509 to direct operation of the pump 504. For example, the controller 502/509 may be operable to receive an input from the sensor 508, wherein the input indicates an automated insulin delivery (AID) application setting. Based on the AID application setting, the controller 502/509 may modify the behavior of the pump 504 and resulting amount of the liquid drug 525 to be delivered to the patient 503 via the device 505.

In some embodiments, the sensor 508 may be, for example, a continuous glucose monitor (CGM). The sensor 508 may be physically separate from the pump 504, or may be an integrated component within a same housing thereof. The sensor 508 may provide the controller 502 with data indicative of measured or detected blood glucose levels of the user.

The power element 523 may be a battery, a piezoelectric device, or the like, for supplying electrical power to the device 505. In other embodiments, the power element 523, or an additional power source (not shown), may also supply power to other components of the pump 504, such as the controller 502, memory, the sensor 508, and/or the needle deployment component 528.

In an example, the sensor 508 may be a device communicatively coupled to the controller 502 and may be operable to measure a blood glucose value at a predetermined time interval, such as approximately every 5 minutes, 10 minutes, or the like. The sensor 508 may provide a number of blood glucose measurement values to the AP application.

In some embodiments, the pump 504, when operating in a normal mode of operation, provides insulin stored in the reservoir 100/200 to the patient 503 based on information (e.g., blood glucose measurement values, target blood glucose values, insulin on board, prior insulin deliveries, time of day, day of the week, inputs from an inertial measurement unit, global positioning system-enabled devices, Wi-Fi-enabled devices, or the like) provided by the sensor 508 or other functional elements of the pump 504. For example, the pump 504 may contain analog and/or digital circuitry that may be implemented as the controller 502/509 for controlling the delivery of the drug or therapeutic agent. The circuitry used to implement the controller 502/509 may include discrete, specialized logic and/or components, an application-specific integrated circuit, a microcontroller or processor that executes software instructions, firmware, programming instructions or programming code enabling, for example, an AP application stored in memory, or any combination thereof. For example, the controller 502/509 may execute a control algorithm and other programming code that may make the controller 502/509 operable to cause the pump to deliver doses of the drug or therapeutic agent to a user at predetermined intervals or as needed to bring blood glucose measurement values to a target blood glucose value. The size and/or timing of the doses may be pre-programmed, for example, into the AP application by the patient 503 or by a third party (such as a health care provider, a parent or guardian, a manufacturer of the wearable drug delivery device, or the like) using a wired or wireless link.

Although not shown, in some embodiments, the sensor 508 may include a processor, memory, a sensing or measuring device, and a communication device. The memory may store an instance of an AP application as well as other programming code and be operable to store data related to the AP application.

In various embodiments, the sensing/measuring device of the sensor 508 may include one or more sensing elements, such as a blood glucose measurement element, a heart rate monitor, a blood oxygen sensor element, or the like. The sensor processor may include discrete, specialized logic and/or components, an application-specific integrated circuit, a microcontroller or processor that executes software instructions, firmware, programming instructions stored in memory, or any combination thereof.

As used herein, the algorithms or computer applications that manage blood glucose levels and insulin therapy may be referred to as an "artificial pancreas" algorithm-based system, or more generally, an artificial pancreas (AP) application. An AP application may be programming code stored in a memory device and that is executable by a processor, controller or computer device.

The techniques described herein for a drug delivery system (e.g., the system 500 or any components thereof) may be implemented in hardware, software, or any combination thereof. Any component as described herein may be implemented in hardware, software, or any combination thereof. For example, the system 500 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/ or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A reservoir of a wearable drug delivery device, the reservoir comprising:
   a housing defining an interior cavity, the housing comprising an inlet and an outlet that communicate with the reservoir through a septum having an end surface with an opening; and
   a flexible liner within the interior cavity, the flexible liner operable to transition between an expanded configuration in which the flexible liner is in a natural expanded state and flush with the end surface of the septum that has the opening before a medicament passes into a liquid chamber of the reservoir, and a collapsed configuration in which the flexible liner buckles, collapses, or folds under the medicament to decrease a volume of the flexible liner as more medicament enters the liquid chamber, wherein the liquid chamber is defined by an exterior of the flexible liner and the interior surface of the housing.

2. The reservoir of claim 1, further comprising a fill port chamber enclosing the inlet of the housing, the fill port chamber comprising a fill needle inlet and an air vent.

3. The reservoir of claim 2, further comprising a self-sealing septum covering the fill needle inlet and a hydrophobic cover covering the air vent.

4. The reservoir of the wearable drug delivery device of claim 2, further comprising a pressure-activated septum coupled to the fill port chamber and the housing, wherein the pressure-activated septum includes a slit operable to fluidly connect the liquid chamber and the fill port chamber.

5. The reservoir of the wearable drug delivery device of claim 1, further comprising a membrane extending across the outlet of the housing.

6. The reservoir of the wearable drug delivery device of claim 5, wherein the outlet comprises an outlet cavity recessed into the interior surface of the housing, wherein the membrane is positioned within the outlet cavity, and wherein the membrane is a polymer mesh.

7. The wearable drug delivery device of claim 5, wherein the outlet comprises:
   a first outlet path extending between the liquid chamber and an outlet chamber, wherein the outlet chamber is located external to an exterior surface of the housing, wherein the membrane is positioned within the outlet chamber, and wherein the membrane is a polymer mesh; and
   a second outlet path extending through an outlet block, wherein the second outlet path is fluidly connected with the outlet chamber.

8. The reservoir of claim 1, wherein the liquid chamber is defined by an entirety of a fluid-containing space within the exterior of the flexible liner and an interior surface of the housing.

\* \* \* \* \*